(12) United States Patent
Gao et al.

(10) Patent No.: US 6,369,589 B1
(45) Date of Patent: Apr. 9, 2002

(54) PERFORATION CORROSION PREDICTION TOOL

(75) Inventors: Guilian Gao, Livonia, MI (US); Mikhail Y. Vlassov, Sant Petersburg (RU)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/510,658

(22) Filed: Feb. 22, 2000

(51) Int. Cl.$^7$ .................. G01R 27/08; G01N 27/00; G01N 17/00
(52) U.S. Cl. .............. 324/693; 324/71.2; 324/700; 422/53
(58) Field of Search .................. 324/693, 700, 324/71.2; 422/53

(56) References Cited

U.S. PATENT DOCUMENTS 4,846,936 A * 7/1989 Tsurumaru et al. ......... 205/791
4,887,025 A * 12/1989 Re Fiorentin et al. ...... 324/693
5,171,524 A * 12/1992 Niolon ..................... 422/53
5,859,537 A    1/1999 Davis et al.

\* cited by examiner

*Primary Examiner*—Safet Metjahic
*Assistant Examiner*—Wasseem H. Hamdan
(74) *Attorney, Agent, or Firm*—Damian Porcari

(57) ABSTRACT

A method for predicting perforation corrosion in a hem flange. The method includes placing an electrode in the hem flange. The electrode extends substantially the entire length of the hem flange. An electrolyte is introduced into the hem flange so that the electrode is immersed, and the electrochemical impedance spectrum of the hem flange is measured. The measured electrochemical impedance spectrum of the hem flange can be compared to a reference electrochemical impedance spectrum. A collection of reference electrochemical impedance spectra can be created by storing the measured electrochemical impedance spectrum of the hem flange.

16 Claims, 4 Drawing Sheets

PERFORATION CORROSION PREDICTION TOOL

BACKGROUND OF THE INVENTION

Perforation corrosion of hem flanges in automobiles and trucks, including door, hood, and decklid hem flanges, is the major source of vehicle corrosion warranty repairs. A hem flange is a technique for joining and sealing edges of sheet metal structures involving at least two sheets of material in which one sheet (the outer sheet) is folded or hemmed to accept the second sheet (the inner sheet). These repairs cost manufacturers millions of dollars every year.

As a result, manufacturers have been working to improve hem flange corrosion performance for many years. The current practice in corrosion engineering is to build test modules or vehicles with the desired attributes, and then run the modules or vehicles through a corrosion chamber test or through a proving ground test. Perforation corrosion is measured by visual inspection, or by physically cutting the hem flanges open and examining the extent of corrosion after a certain period of time in the field, in the proving ground, or in the corrosion chamber. At best, these studies provide a qualitative comparison among different materials and systems. The test methods measure corrosion after it occurs, rather than predicting whether it will occur. These test procedures take a long time (about 10 to 12 months) and are very expensive (approximately $100,000 per vehicle).

It is well known that manufacturing process variations contribute to the poor corrosion performance of many vehicles. Among the process variables believed to contribute to corrosion performance are variation in hem flange opening, the precision of the structure adhesive application, and E-coat (electrolytic or electrophoretic coating) bake temperature. However, the high cost of performing the current corrosion tests prohibits running tests with a statistically significant sample size in order to collect enough data to quantify and evaluate the significance of each process variable using the present methods.

U.S. Pat. No. 5,859,537 discloses a non-destructive method for evaluating corrosion on painted metal surfaces. However, the sensor used is relatively small, approximately 1 cm$^2$ in contact with the coated metal surface. Thus, the results only reflect conditions in close proximity to the sensor. It will not allow evaluation of the entire length of the hem flange.

Therefore, there is a need for a simple, non-destructive method of predicting perforation corrosion performance. The test should be quick and inexpensive, and it should also allow evaluation of the entire hem flange.

SUMMARY OF THE INVENTION

These needs are met by the present invention which is a method for predicting perforation corrosion in a hem flange. The method includes placing an electrode in the hem flange. The electrode extends substantially the entire length of the hem flange. An electrolyte is introduced into the hem flange so that the electrode is immersed, and the electrochemical impedance spectrum of the hem flange is measured. The measured electrochemical impedance spectrum of the hem flange can be compared to a reference electrochemical impedance spectrum. A collection of reference electrochemical impedance spectra can be created by storing the measured electrochemical impedance spectrum of the hem flange.

Accordingly, it is an object of the present invention to provide a fast, inexpensive, non-destructive method for predicting perforation corrosion along the length of a hem flange.

DETAILED DESCRIPTION OF THE INVENTION

Figure 1:
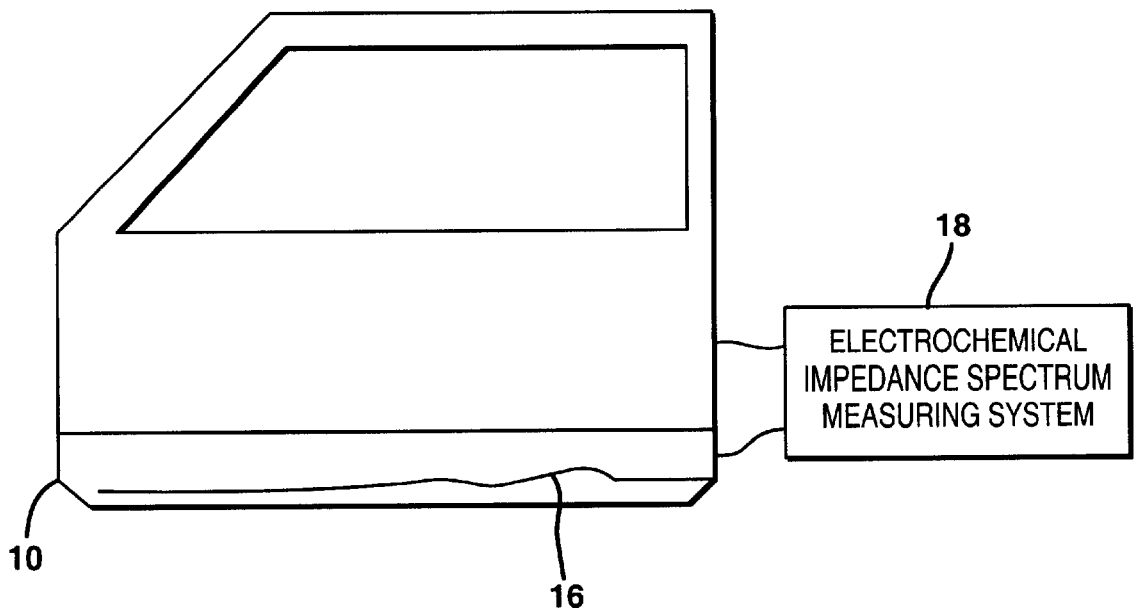
FIG. 1 is a schematic diagram showing a door hem flange being measured according to the present invention.
Figure 2:
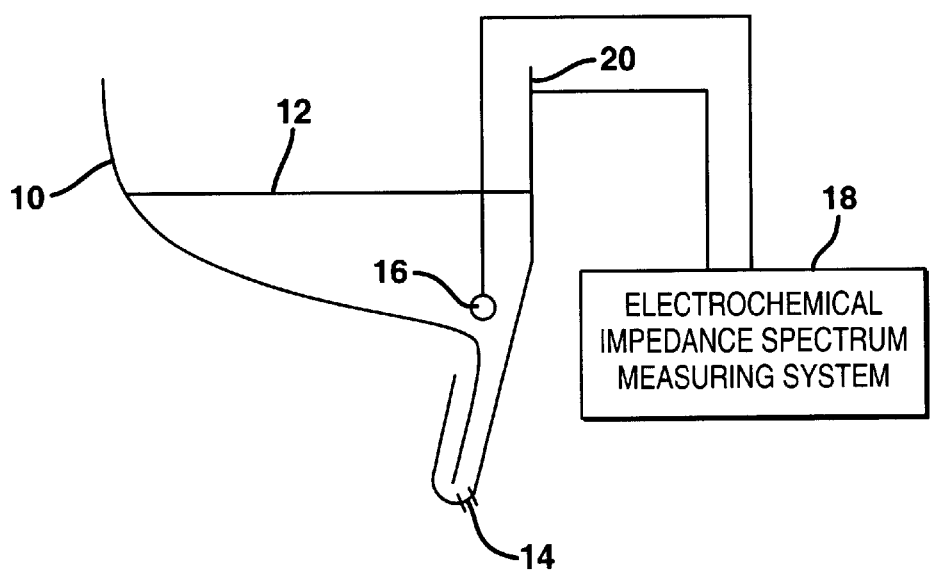
FIG. 2 is a cross-section of the schematic of FIG. 1.

As shown in FIGS. 1 and 2, an electrode 16 is placed in the hem flange 10. The electrode 16 extends substantially the entire length of the hem flange to be measured, for example, the bottom of the door. This allows evaluation of the entire hem flange, not just a small portion of it. The electrode 16 is preferably made of a noble metal, such as platinum or gold. An electrolyte 12 is introduced into the door hem flange 10 to a depth so that the electrode 16 is immersed, preferably completely. The electrolyte is preferably water, and tap water can be used. If there are drain holes 14 in the hem flange 10, they are temporarily blocked in order to allow the water to fill in the hem flange. The electrode is connected to the electrochemical impedance spectrum (EIS) measuring system 18. The EIS measuring system 18 is also connected to the door panel 20. The EIS of the hem flange can then be measured in a matter of hours. A portable unit, suitable for data collection in the field or in assembly plants, can be used for the EIS measurement. When the measurement is complete, the drain holes 14 are reopened, and the electrode is removed.

Figure 3:
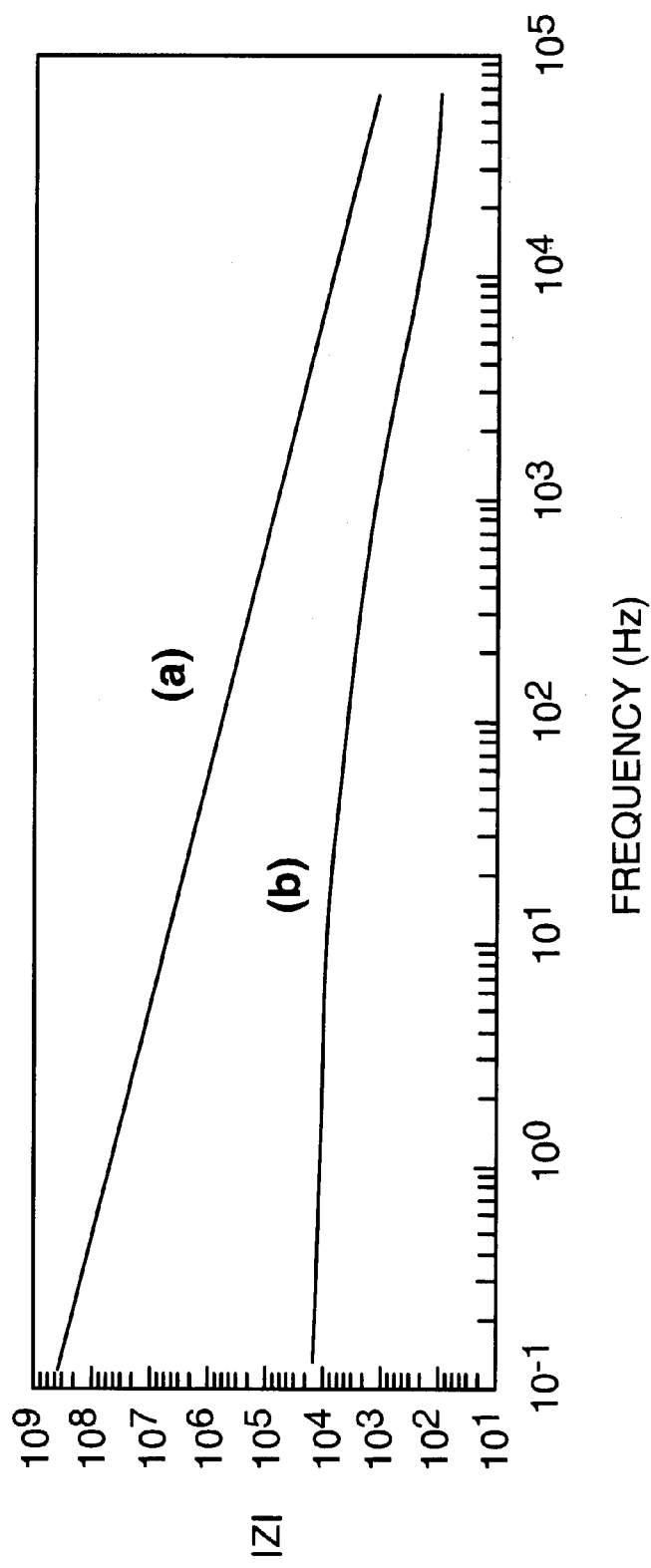
FIGS. 3–5 are graphs showing a comparison of the electrochemical impedance response for an area with good E-coat coverage and inside a door hem flange.
Figure 4:
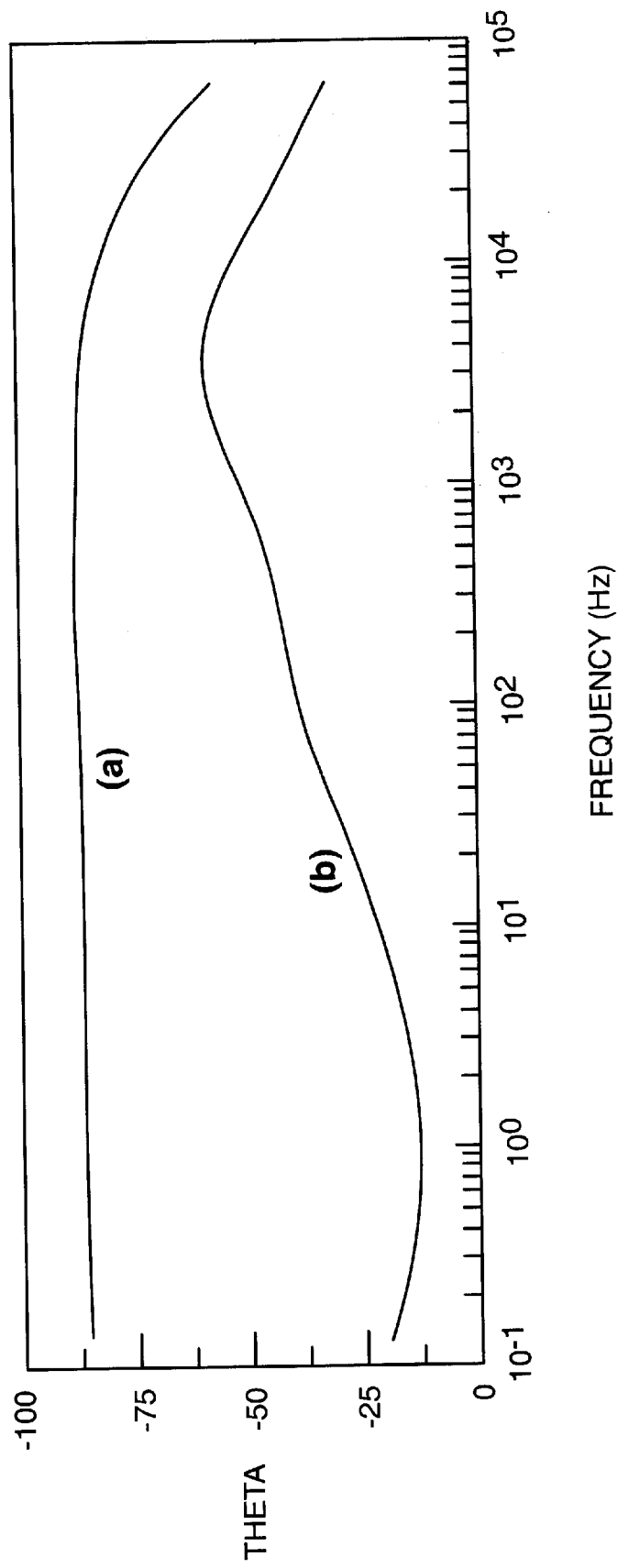
Figure 5:
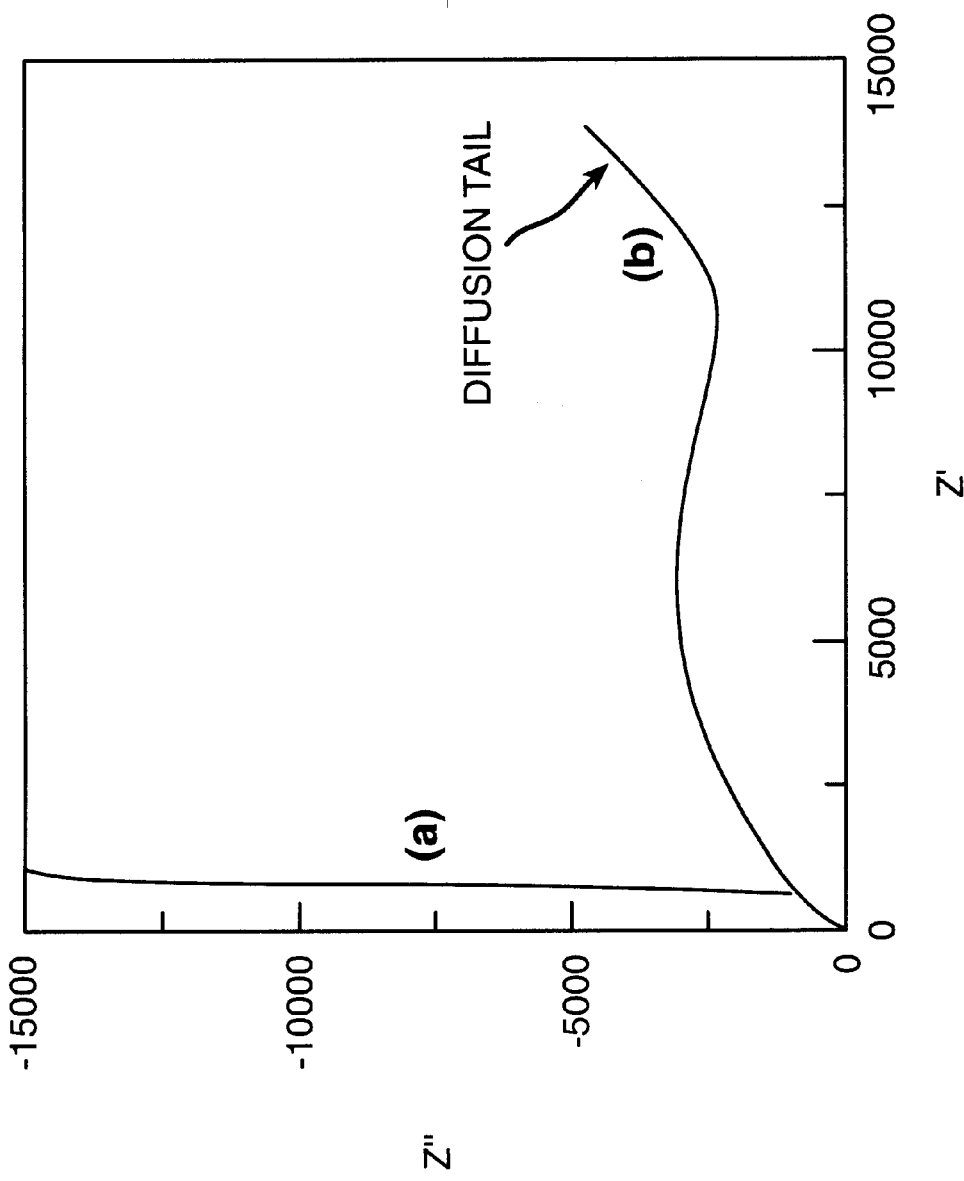

The EIS is related to the condition of phosphate and E-coat inside the hem flanges and thus can be used to predict the corrosion performance of the vehicle in the field. EIS measurements have been conducted on artificial and real truck door hem flanges using the methodology of the present invention. For coated metal surfaces, the impedance is much lower on surfaces with poor and/or incomplete coatings than on well protected surfaces. FIGS. 3–5 show a comparison of impedance on a surface with good E-coat coverage and that inside a door hem flange. These results reveal the existence of a very porous E-coat with bare metal surfaces exposed inside the hem flanges, as is evident from the very low value of impedance and the existence of the diffusion tail at the low frequencies.

The present invention requires only one measurement in each hem flange in a brand-new vehicle in order to predict its corrosion performance. The measurement does not use any undesirable chemicals or cause any irreversible changes to the hem flange. Therefore, it is completely non-destructive. The test cycle time is also very short (only a few hours), and the cost is very low.

These features make it possible to measure large numbers of vehicles to obtain a statistically significant data set to evaluate the factors which contribute to corrosion performance quickly and inexpensively. The method can also be used as a process monitoring and quality control tool for manufacturing process variables, such as adhesive dispensing, phosphate, and E-coat processes. In addition, the method can also be used as a valuable tool for assessing and monitoring progress of corrosion inside the hem flange in the field. The improved understanding of corrosion which this method provides may ultimately result in a more cost effective means of improving corrosion resistance in hem flanges.

While certain representative embodiments and details have been shown for purposes of illustrating the invention, it will be apparent to those skilled in the art that various changes in the compositions and methods disclosed herein may be made without departing from the scope of the invention, which is defined in the appended claims.

What is claimed is:

1. A method for measuring an electrochemical impedance spectrum of a hem flange comprising:
   placing an electrode in the hem flange;
   introducing an electrolyte into the hem flange so that the electrode is immersed; and
   measuring the electrochemical impedance spectrum of the hem flange.

2. The method of claim 1 further comprising comparing the measured electrochemical impedance spectrum of the hem flange to a reference electrochemical impedance spectrum.

3. The method of claim 1 further comprising storing the measured electrochemical impedance spectrum of the hem flange to create a collection of reference electrochemical impedance spectra.

4. The method of claim 3 further comprising comparing the measured electrochemical impedance spectrum to the collection of reference electrochemical impedance spectra.

5. The method of claim 1 wherein said electrode extends substantially the entire length of the hem flange.

6. The method of claim 5 wherein the electrode comprises a noble metal.

7. The method of claim 6 wherein the noble metal is selected from platinum, and gold.

8. The method of claim 1 further comprising temporarily blocking a drain hole in the hem flange before introducing the electrolyte into the hem flange.

9. The method of claim 1 wherein the electrolyte comprises water.

10. A method for measuring an electrochemical impedance spectrum of a hem flange comprising:
    placing an electrode in the hem flange, the electrode extending substantially the entire length of the hem flange;
    introducing an electrolyte into the hem flange so that the electrode is immersed;
    measuring the electrochemical impedance spectrum of the hem flange;
    comparing the measured electrochemical impedance spectrum of the hem flange to a reference electrochemical impedance spectrum;
    removing the electrolyte from the hem flange; and
    removing the electrode from the hem flange.

11. The method of claim 10 further comprising storing the measured electrochemical impedance spectrum of the hem flange to create a collection of reference electrochemical impedance spectra.

12. The method of claim 11 wherein the collection of reference electrochemical impedance spectra includes the reference electrochemical impedance spectrum.

13. The method of claim 10 wherein the electrode comprises a noble metal.

14. The method of claim 13 wherein the noble metal is selected from platinum, and gold.

15. The method of claim 10 further comprising temporarily blocking a drain hole in the hem flange before introducing the electrolyte into the hem flange.

16. The method of claim 10 wherein the electrolyte comprises water.

* * * * *